United States Patent [19]
Yng-Wong

[11] Patent Number: 5,834,000
[45] Date of Patent: Nov. 10, 1998

[54] ANTIVIRAL AND ANTIMICROBIAL HERBAL COMPLEX

[76] Inventor: Quing Non Yng-Wong, 5524 MacArthur Blvd., Washington, D.C. 20016

[21] Appl. No.: 837,336

[22] Filed: Apr. 11, 1997

[51] Int. Cl.⁶ .................................................. A01N 25/00
[52] U.S. Cl. ........................................ 424/405; 424/195.1
[58] Field of Search ................................ 424/405, 195.1

[56] References Cited

PUBLICATIONS

Cheng et al CN 1080871 Jan. 19, 1994.
Jiang CN 1105581, Jul. 1995.
Chinese Herbal Medicine, Bensky et al, Eastland Press, 1986, pp. 66–67.
Chinese Herbology, Dharmananda, Institute for Traditional Medicine . . . , 1992, pp. 120, 139, 161, 238, 439.
Chinese Herbal Patent Formulas; Fratkin; 1986; Shya Publications, Santa Fe, New Mexico; pp. 52, 53, and 57.

*Primary Examiner*—Neil S. Levy
*Attorney, Agent, or Firm*—Nixon & Vanderhye P.C.

[57] ABSTRACT

A pharmacologically effective composition of herbs is provided which is antiviral, antibacterial, and symptom relieving for colds, flu, sinus infections, stomach infections, blocked ears due to infection, bronchitis, genital herpes, and herpes simplex. The composition does not contain any undesirable stimulants or other ingredients, such as caffeine and chlorohydrate. The preferred composition includes Isatis leaf and root, as well as other anti-microbial herbal agents, along with herbs for aches, pains, sore throat, and to reduce fever.

16 Claims, No Drawings

ANTIVIRAL AND ANTIMICROBIAL HERBAL COMPLEX

BACKGROUND AND SUMMARY OF THE INVENTION

Colds and influenza are major causes of illness and loss of productivity throughout the United States and the rest of the world. For example the National Center for Health Statistics estimates that in 1992 62 million cases of the common cold in the United States required medical attention, and that colds caused 157 million days of restricted activity and 15 million days lost from work. Approximately 10–15% of adult colds are caused by viruses also responsible for other serious illnesses, including influenza A & B viruses. It has long been considered desirable to provide an effective treatment for a wide variety of illnesses caused by viruses and bacterium, that are potent antiviral and antimicrobial agents, but also can relieve symptoms. Some traditional Chinese medicine herbal formulas can be at least somewhat effective in this regard, but they typically contain caffeine, chlorohydrate, or other components undesirable to a large segment of the population. It is desirable to provide effective herbal compositions without caffeine or other stimulants, and without chlorohydrate or like compositions.

According to the present invention a pharmacologically effective composition which is a broad spectrum antiviral and antimicrobial is provided which is completely herbal in nature and does not contain caffeine, chlorohydrate, or like undesirable components. Isatis leaf and root are the major ingredients, comprising collectively a majority of the composition. The composition may be used in the treatment of colds, infections, mumps, hepatovirus, chronic fatigue, influenza, sinus infections, stomach infections, blocked ears due to infection, bronchitis, genital herpes, and herpes simplex. The compositions according to the present invention are antiviral, antibacterial, and symptom relieving.

According to one aspect of the present invention a pharmacologically effective composition is provided comprising as the active ingredients: a mixture of *Isatides tinctoria radix, Isatides tinctoria folium, Pueraria lobata radix, Forsythia suspensa fructus, Lonicera japonica flos* and *Chrysanthemem indici flos,* in a pharmacologically effective amount. The components of the mixture preferably have the following contributions expressed in approximate weight percent:

*Isatides tinctoria radix* 32.5–42.5% (e.g. about 37.5%)
*Isatides tinctoria folium* 32.5–42.5% (e.g. about 37.5%)
*Pueraria lobata radix* 8–12% (e.g. about 10%)
*Forsythia suspensa fructus* 3–7% (e.g. about 5%)
*Lonicera japonica flos* 3–7% (e.g. about 5%)
Chrysanthemem indici flos 3–7% (e.g. about 5%).

Preferably the composition active ingredients consist essentially of the herbs set forth above.

The invention also relates to a method of substantially eliminating or ameliorating viral and microbial illness of human patients comprising the step of administering to a human patient in need of treatment an effective amount of a pharmacological composition such as set forth above. The invention also relates to a method of substantially eliminating or ameliorating in a human patient colds, flu, sinus infections, stomach infections, blocked ears due to infection, bronchitis, genital herpes, and herpes simplex, comprising the step of administering to a human patient in need of treatment an effective amount of a pharmacological composition as set forth above.

The invention also relates to a method of substantially eliminating or ameliorating viral and microbial illness of human patients comprising the step of administering to a human patient a pharmacologically effective composition comprising active ingredients consisting essentially of Isatis leaf and root making up the majority of the active ingredients, along with other anti-microbial herbal agents, and herbal agents for relief of aches and pains, sore throat, and to reduce fever.

DETAILED DESCRIPTION OF THE PREFERRED EMBODIMENT

The identification of specific herbal complexes that will perform effectively pharmacologically without severe side effects is a painstaking and time consuming endeavor both in the initial development of the formulation, and in its subsequent testing. Traditional Chinese medicine includes a number of formulas that can be effective for the treatment of certain illnesses, however those formulas do not necessarily transfer over to other populations with the same effectiveness, and oftentimes can contain undesirable components (such as caffeine and chlorohydrate) for a large portion of the population.

According to the present invention a broad spectrum antiviral and antimicrobial herbal composition is provided which has been found to be effective in the treatment of Western population and it does not contain undesirable ingredients such as caffeine and chlorohydrate. The compositions according to the present invention use Isatis leaf and root as the major ingredients. These herbs have been used in traditional Chinese medicine for colds, virus, infection, cancer, mumps, hepatovirus, and chronic fatigue. These components are utilized in the composition according to the present invention along with other potent herbal antimicrobial agents, and along with herbs for relief of aches and pains, and sore throat, and to reduce fevers. The herbal compositions according to the present invention are antiviral, antibacterial, and symptom relieving.

According to the present invention a pharmacologically effective composition is provided comprising as active ingredients a mixture of *Isatides tinctoria radix, Isatides tinctoria folium, Pueraria lobata radix, Forsythia suspensa fructus, Lonicera japonica flos* and *Chrysanthemem indici flos,* in a pharmacologically effective amount. The components of the mixture preferably have the following contributions expressed in approximate weight percent:

| Isatides tinctoria radix | 32.5–42.5% (e.g. about 37.5%) |
|---|---|
| Isatides tinctoria folium | 32.5–42.5% (e.g. about 37.5%) |
| Pueraria lobata radix | 8–12% (e.g. about 10%) |
| Forsythia suspensa fructus | 3–7% (e.g. about 5%) |
| Lonicera japonica flos | 3–7% (e.g. about 5%) |
| Chrysanthemem indici flos | 3–7% (e.g. about 5%). |

"*Isatides tinctoria radix*" is also known as indigo, or cruciferae, or Radix Isatidis, whereas "*Isatides tinctoria folium*" is also known as indigo, cruciferae, and folium Isatides. Active ingredients are believed to be indirubin, sinigrin, indical, indoxyl, isatan, and labenzyme.

"*Pueraria lobata radix*" is also known as Pueraria, leguminosae, radix puerariae, and by the common name "kudzu". Active ingredients are believed to be daidzin, daizein, and puerarin. In the composition according to the invention it relieves fever, congestion, and other symptoms, without undesirable side effects.

"*Forsythia suspensa fructus*" comprises halfshells of the fruit of forsythia, also known as fructose forsythiae, and Oleaceae. Active constituents are believed to be phillyrin and other saponin and flavonol glycosides. In the composition of the invention it relieves the symptoms of sore throat and reduces fever without undesirable side effects.

"*Lonicera japonica flos*" comprises the whole flower buds of Lonicera, also known as Flos Lonicerae, and Caprifolaceae. Active ingredients are believed to be luteolin glucoside, lonicerin, and inositol. This herb is a potent anti-microbial and also relieves the symptoms of sore throat, and can reduce fever.

"*Chrysanthemem indici flos*" is also known as the whole flowers of chrysanthemum, or Flos Chrysanthemi, or Compositae. Active constituents are believed to be apigenin, borneol, and a variety of paraffins. In the compositions according to the invention this herbal agent soothes a number of aches, pains, and other symptoms of colds, flu, and the like, without side effects.

In addition to the active ingredients, the herbal complexes utilized according to the present invention may have any number of substantially inert ingredients which will vary depending upon the particular form by which the complex will be administered. Normally the complex is administered in the form of ingestible tablets or capsules which are swallowed with water, although the complex active ingredients may be mixed with food or beverage items and eaten or drunk, or in extreme cases may be introduced directly into the bloodstream using a hypodermic needle, I.V., or the like. The dose may vary depending upon the size, age, and condition of the patient being treated and the particular percentages of components herbal complex utilized, but normally between about 500–3000 mg of active herbal complex is administered per day, with part of the total dose preferably taken at two or more different times during the day.

A typical manner of processing herbs to produce the complex may be as follows, although a wide variety of different known processing techniques may be utilized depending upon the exact form of the material desired, and the availability of material or equipment:

The powder end product of the complex is typically a 1:1 extract. Testing of raw materials used is conducted using standard organoleptic, High performance Liquid Chromatography, and microbiologic methods. The solvent mixture used for extractions for herbs used in the complex is about 95% SDA-3C and about 5% potable water. SDA-3C is specifically denatured alcohol composed of 95% ethanol and 5% isopropyl. The extraction method is thermokinetic maceration, specifically about 180° F. for about three hours, plus warm up and cool down.

Following extraction, a sample is tested for the percentage of dissolved solids recovered. This is compared with the specified standards and, when necessary, the processing is continued until the standards are reached. The base material of the extract is marc; no rinse of the extracted powder is required. The miscella is distilled. The distilled total miscella is dehydrated onto the base material. This receives a final milling (1/32" screen) in a sanitary stainless mill, using a vacuum system to transport the product directly into the final containers. Samples are taken for quality control tests which are visual, taste, microbiologic and High Performance Liquid chromatography. Samples are also taken for permanent record. That material is readily made into tablets, or placed in ingestible capsules, e.g. about 300 mg per capsule.

Another possible technique is as follows:

The powder and end product of this formula is typically a 1:1 extract. Testing of raw materials used is conducted using standard organoleptic, High Performance Liquid Chromatography and microbiologic methods. The solvent solution is preferably about 95% SDA-3C and 5% water.

The herb and the solvent are added together in the extract processor for processing. The supernatant liquid of solvent and solids is drained into the holding/settling tank where the volume is measured and the solids content is determined by analysis. Samples are drawn of both and liquid supernatant and sediment for microbiologic testing. The supernatant liquid is pumped through a 100 mesh liquid filter into the Sanitizing vessel. The liquid is processed for a minimum of four hours at the boiling temperature of about 178° F. The volume of the liquid is measured and a solids analysis is done. A sample is drawn for microbiologic testing. The liquid is pumped through a 100 mesh filter and sprayed into the vacuum dryer, using volume and solids data to adjust the product to the desired concentration for the finished product. The resulting material is dried. The processor is emptied into sanitary bulk bins or barrels and transported to milling. A pre-grind sample is drawn for biologic testing. The material is milled in a sanitary stainless steel milling system using a 1/16" screen. The material is unloaded from the mill system directly via Vac-u-Max collector into double lined 44 gallon fiber drums. A sample is drawn from each container for biologic testing. Typical microbiologic requirements are:

|  | Limits |
| --- | --- |
| Aerobes | max. 10,000/g |
| Coliform | negative |
| Salmonella | negative |
| *E. Coli* | negative |
| Yeast | max. 100/g |
| Mold | max. 100/g |

The utilization of complex herbal formulations as set forth above for the elimination or amelioration of a number of viral or bacteria related illnesses, such as colds, flu, sinus infections, stomach infections, blocked ears due to infections, bronchitis, genital herpes, and herpes simplex, has been shown to be effective through testing. A pharmacologically effective composition comprising as active ingredients a mixture having the following contributions expressed in weight percent:

| Isatides tinctoria radix | about 37.5% |
| --- | --- |
| Isatides tinctoria folium | about 37.5% |
| Pueraria lobata radix | about 10% |
| Forsythia suspensa fructus | about 5% |
| Lonicera japonica flos | about 5% |
| Chrysanthemem indici flos | about 5%, | has been tested as indicated by the following table (each capsule contained about 300 mg active ingredients):

Clinical Data Table

| Log # | Patient Age & Gender | Dosage Time | Treatment Duration | Presenting Symptoms | Resultant Effects | Side Effects |
|---|---|---|---|---|---|---|
| 304 | 54 yrs female | 1 capsule 3 × daily | 10 days | stomach "flu" | stomach much improved | none |
| 305 | late 50s male | 1 capsule 3 × daily | 3 weeks | bacterial infection in his stomach | "it is the only medication that worked on his stomach problem" | none |
| 306 | mid 30s male | 3 capsules 3 × daily | 5 days | residual ear blockage after the flu | his ears completely cleared up | none |
| 308 | 49 years male | 2 capsules 3 × daily | 1 week | chronic bronchitis since 1973 | bronchitis cleared up | none |

In the above table, each capsule contained approximately 300 mg of the herbal complex. The herbal formulations according to the invention are effective when administered alone, but can be administered with other pharmacological treatments typically without adverse side effects.

It is highly desirable that the herbal compositions according to the present invention consist essentially of herbal agents, and do not have undesirable materials such as those that are primarily stimulants, depressants, or the like, as active ingredients (and that any "inert" ingredients added also do not include undesirable materials such as depressants or stimulants). Particularly to be avoided are stimulants such as caffeine, and chlorohydrate or like materials.

Thus it will be seen that according to the present invention broad spectrum antiviral and antimicrobial herbal complexes are provided which are effective but which have few or no side effects, and do not require stimulants or other undesirable ingredients to be effective. While the invention has been herein shown and described in what is presently conceived to be the most practical and preferred embodiment thereof it will be apparent to those of ordinary skill in the art that many modifications may be made thereof within the scope of the invention, which scope is to be accorded the broadest interpretation of the appended claims so as to encompass all equivalent methods and products.

What is claimed is:

1. A pharmacologically effective composition comprising as active ingredients a mixture of *Isatides tinctoria radix, Isatides tinctoria folium, Pueraria lobata radix, Forsythia suspensa fructus, Lonicera japonica flos* and *Chrysanthemem indici flos*, in a pharmacologically effective amount, wherein the components of the mixture have the following contributions expressed in approximate weight percent:

| | |
|---|---|
| Isatides tinctoria radix | 32.5–42.5% |
| Isatides tinctoria folium | 32.5–42.5% |
| Pueraria lobata radix | 8–12% |
| Forsythia suspensa fructus | 3–7% |
| Lonicera japonica flos | 3–7% |
| Chrysanthemem indici flos | 3–7%. |

2. A composition as recited in claim 1 wherein said active ingredients consist essentially of *Isatides tinctoria radix, Isatides tinctoria folium, Pueraria lobata radix, Forsythia suspensa fructus, Lonicera japonica flos* and *Chrysanthemem indici flos*.

3. A composition as recited in claim 2 wherein the components of the mixture have the following contributions expressed in approximate weight percent:

| | |
|---|---|
| Isatides tinctoria radix | 32.5–42.5% |
| Isatides tinctoria folium | 32.5–42.5% |
| Pueraria lobata radix | 8–12% |
| Forsythia suspensa fructus | 3–7% |
| Lonicera japonica flos | 3–7% |
| Chrysanthemem indici flos | 3–7%. |

4. A method of substantially eliminating or ameliorating viral and microbial illness of human patients comprising the step of administering to a human patient in need of treatment an effective amount of the pharmacological composition of claim 1.

5. A method of substantially eliminating or ameliorating viral and microbial illness of human patients comprising the step of administering to a human patient in need of treatment an effective amount of the pharmacological composition comprising as active ingredients a mixture of *Isatides tinctoria radix, Isatides tinctoria folium, Pueraria lobata radix, Forsythia suspensa fructus, Lonicera japonica flos* and *Chrysanthemem indici flos*, in a pharmacologically effective amount.

6. A method of substantially eliminating or ameliorating viral and microbial illness of human patients comprising the step of administering to a human patient in need of treatment an effective amount of the pharmacological composition of claim 2.

7. A method of substantially eliminating or ameliorating viral and microbial illness of human patients comprising the step of administering to a human patient in need of treatment an effective amount of the pharmacological composition of claim 3.

8. A method of substantially eliminating or ameliorating in a human patient colds, flu, sinus infections, stomach infections, blocked ears due to infection, bronchitis, genital herpes, and herpes simplex, comprising the step of administering to a human patient in need of treatment an effective amount of the pharmacological composition of claim 1.

9. A method of substantially eliminating or ameliorating in a human patient colds, flu, sinus infections, stomach infections, blocked ears due to infection, bronchitis, genital herpes, and herpes simplex, comprising the step of administering to a human patient in need of treatment an effective amount of the pharmacological composition comprising as active ingredients a mixture of *Isatides tinctoria radix, Isatides tinctoria folium, Pueraria lobata radix, Forsythia suspensa fructus, Lonicera janonica flos* and *Chrysanthemem indici flos*, in a pharmacologically effective amount.

10. A method of substantially eliminating or ameliorating in a human patient colds, flu, sinus infections, stomach infections, blocked ears due to infection, bronchitis, genital herpes, and herpes simplex, comprising the step of administering to a human patient in need of treatment an effective amount of the pharmacological composition of claim 2.

11. A method of substantially eliminating or ameliorating in a human patient colds, flu, sinus infections, stomach infections, blocked ears due to infection, bronchitis, genital herpes, and herpes simplex, comprising the step of administering to a human patient in need of treatment an effective amount of the pharmacological composition of claim 3.

12. A composition as recited in claim 1 wherein the components of the mixture have the following contributions expressed in weight percent:

| | |
|---|---|
| Isatides tinctoria radix | about 37.5% |
| Isatides tinctoria folium | about 37.5% |
| Pueraria lobata radix | about 10% |
| Forsythia suspensa fructus | about 5% |
| Lonicera japonica flos | about 5% |
| Chrysanthemem indici flos | about 5%. |

13. A composition as recited in claim 2 wherein the components of the mixture have the following contributions expressed in weight percent:

| | |
|---|---|
| Isatides tinctoria radix | about 37.5% |
| Isatides tinctoria folium | about 37.5% |
| Pueraria lobata radix | about 10% |
| Forsythia suspensa fructus | about 5% |
| Lonicera japonica flos | about 5% |
| Chrysanthemem indici flos | about 5%. |

14. A method of substantially eliminating or ameliorating viral and microbial illness of human patients comprising the step of administering to a human patient a pharmacologically effective composition having active ingredients consisting essentially of Isatides leaf and root making up the majority of the active ingredients, along with other anti-microbial herbal agents, and herbal agents for relief of aches and pains, sore throat, and to reduce fever.

15. A method as recited in claim 14 wherein said method is practiced by administering a pharmacologically effective composition in which the Isatides leaf and root collectively comprise between 65–85% of the active ingredients.

16. A method of substantially eliminating or ameliorating viral and microbial illness of human patients comprising the step of administering to a human patient a pharmacologically effective composition comprising active ingredients comprising Isatides leaf and root making up the majority of the active ingredients, along with other anti-microbial herbal agents, and herbal agents for relief of aches and pains, sore throat, and to reduce fever; and wherein said composition is devoid of caffeine or like stimulants, and devoid of chlorohydrate or like compositions.

\* \* \* \* \*